United States Patent [19]
Kraff et al.

[11] Patent Number: 5,667,489
[45] Date of Patent: Sep. 16, 1997

[54] EXPANSILE SURGICAL SLEEVE APPARATUS AND METHOD FOR USING SAME

[76] Inventors: Colman Ross Kraff, 1011 Saxony, Highland Park, Ill. 60035; Manus Colman Kraff, 180 E. Pearson, Chicago, Ill. 60611

[21] Appl. No.: 391,343

[22] Filed: Feb. 21, 1995

[51] Int. Cl.$^6$ .................. A61B 17/20; A61B 17/22; A61M 1/00; A61F 9/00
[52] U.S. Cl. .................. 604/22; 604/35; 606/107; 606/128
[58] Field of Search .................. 604/19, 22, 27, 604/28, 30, 32–35, 39, 40, 43, 48, 49, 51, 96; 606/6, 107, 128, 169, 171; 607/96, 97; 128/661.06, 662.03, 662.06; 623/6

[56] References Cited

U.S. PATENT DOCUMENTS

| | | | |
|---|---|---|---|
| 3,589,363 | 6/1971 | Banko et al. | 128/276 |
| 3,598,119 | 8/1971 | White | 128/215 |
| 4,041,947 | 8/1977 | Weiss et al. | 128/276 |
| 4,223,676 | 9/1980 | Wuchinich et al. | 128/276 |
| 4,465,470 | 8/1984 | Kelman | 604/27 |
| 4,504,264 | 3/1985 | Kelman | 604/22 |
| 4,515,583 | 5/1985 | Sorich | 604/22 |
| 4,538,611 | 9/1985 | Kelman | 128/305 |
| 4,637,401 | 1/1987 | Johnston | 128/663 |
| 4,689,040 | 8/1987 | Thompson | 604/22 |
| 4,705,500 | 11/1987 | Reimal et al. | 604/35 |
| 4,816,017 | 3/1989 | Hood et al. | 604/22 |
| 4,897,079 | 1/1990 | Zaleski et al. | 604/22 |
| 4,921,483 | 5/1990 | Wijay et al. | 604/96 |
| 5,024,668 | 6/1991 | Peters et al. | 606/194 |
| 5,038,756 | 8/1991 | Kepley | 128/24 |
| 5,084,009 | 1/1992 | Mackool | 604/22 |
| 5,084,012 | 1/1992 | Kelman | 604/35 |
| 5,135,481 | 8/1992 | Nemeh | 604/22 |
| 5,151,084 | 9/1992 | Khek | 604/22 |
| 5,188,589 | 2/1993 | Wypych et al. | 604/22 |
| 5,242,449 | 9/1993 | Zaleski | 606/107 |
| 5,282,786 | 2/1994 | Ureche | 604/22 |
| 5,286,256 | 2/1994 | Mackool | 604/22 |
| 5,295,994 | 3/1994 | Bonutti | 606/192 |
| 5,326,342 | 7/1994 | Pflueger et al. | 604/22 |
| 5,344,395 | 9/1994 | Whalen et al. | 604/22 |
| 5,409,444 | 4/1995 | Kensey et al. | 600/18 |
| 5,413,558 | 5/1995 | Paradis | 604/101 |
| 5,464,389 | 11/1995 | Stahl | 604/22 |
| 5,474,530 | 12/1995 | Passafaro et al. | 604/22 |
| 5,498,240 | 3/1996 | Bagaoisan et al. | 604/96 |

OTHER PUBLICATIONS

Product Brochure, "Microseal the Next Generation Surgical Technique", 1 page, date unknown, published by Storz Instruments, Inc.

Richard J. Mackool, "Phaco Handpiece Challenges IOL Technology", Oral Surgery News, May 1, 1993, vol. 11, No. 9, 2 pages.

Product Brochure, "Micro–Incision Phaco: The Next Level", Richard Mackool, date unknown.

*Primary Examiner*—Robert A. Hafer
*Assistant Examiner*—Deborah B. Blyveis
*Attorney, Agent, or Firm*—Dick & Harris

[57] ABSTRACT

A sleeve apparatus for use in combination with a surgical instrument for the removal of a cataract through an incision in a patient's eye. The sleeve apparatus includes a first sleeve member having an interior longitudinal bore through which at least a portion of the surgical instrument is insertable. A second sleeve member, substantially concentric to and operatively attached to an outer surface of the first sleeve member, substantially surrounds a portion of the first sleeve member to create a chamber for receipt of expansion material therebetween. The second sleeve member is resilient and expansile in circumference due to the presence of expansion material within the chamber, so as to substantially conform to the shape of the incision and/or the interior of the wound and substantially seal the incision and reduce the loss of fluid from the patient's eye during surgery.

24 Claims, 4 Drawing Sheets

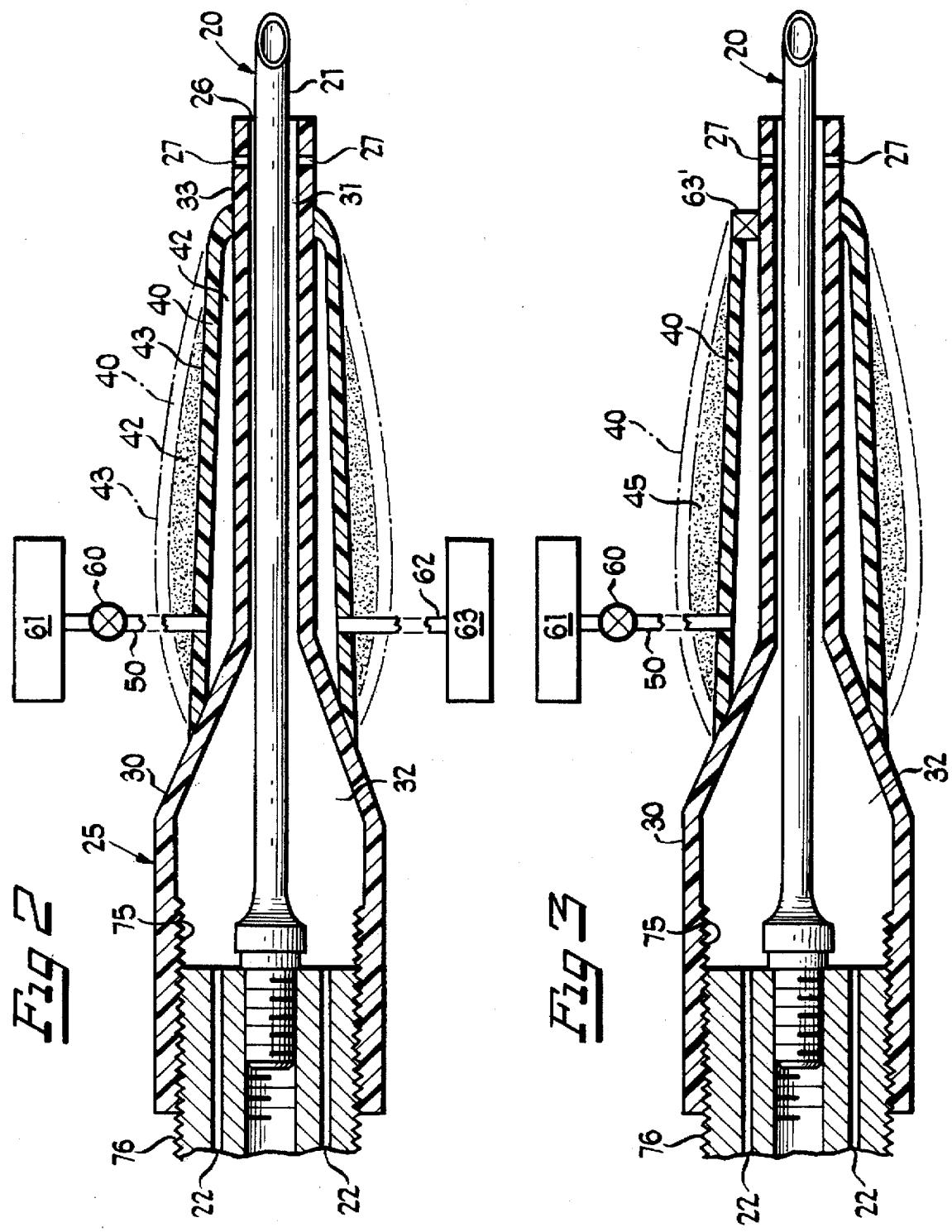

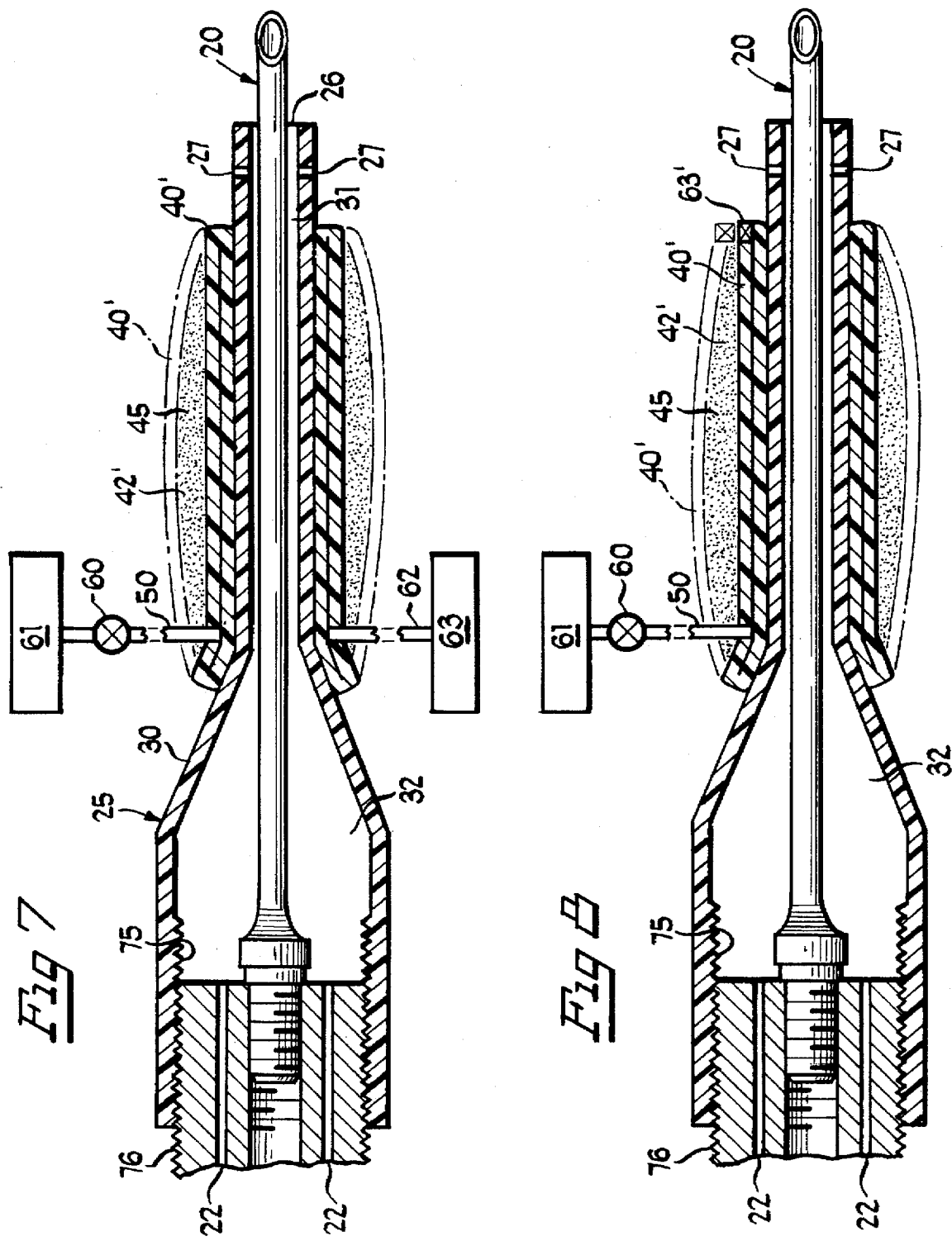

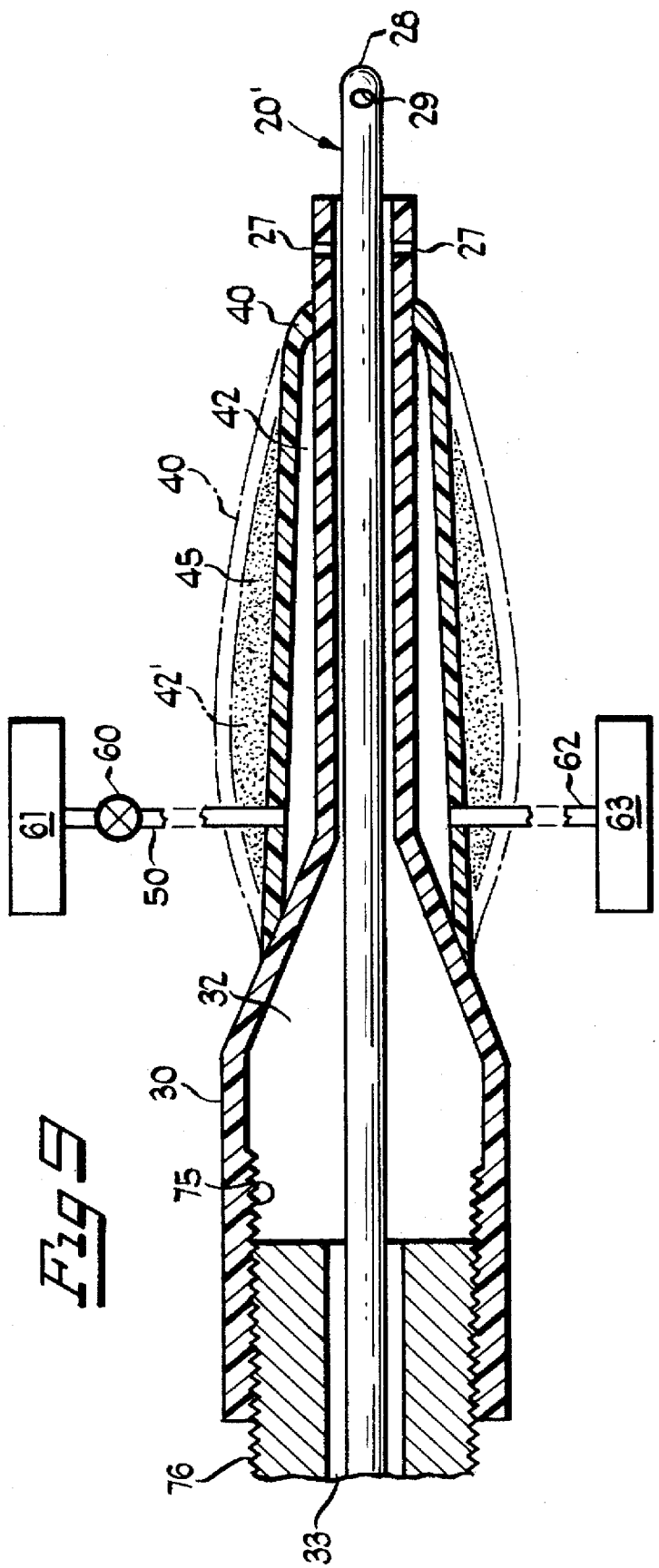

EXPANSILE SURGICAL SLEEVE APPARATUS AND METHOD FOR USING SAME

BACKGROUND OF THE INVENTION

The present invention relates in general to surgical instruments, and, more particularly, to a sleeve apparatus for use in combination with a surgical instrument for removing a cataract through an incision in a patient's eye.

Cataracts, an opacity of the lens of the human eye, are commonly treated by performing a lensectomy, or cataract extraction, followed by replacement of the removed lens with an intraocular lens implant. Surgical instruments for performing a cataract extraction, such as phacoemulsification instruments, are well-known in the art, as shown by Banko et al, U.S. Pat. No. 3,589,363. These phacoemulsification instruments typically include a cutting tip, or needle. The needle is inserted through an incision in the patient's scleral/corneal junction in order to engage the lens. The needle is then caused to be vibrated, such as by ultrasonic vibrations, in order to emulsify the lens. As the lens is emulsified it is removed, by vacuum pressure, through a central bore within the cutting tip or needle. Inasmuch as a significant quantity of heat may be generated from the ultrasonic vibrations, a sleeve is commonly placed around a portion of the needle in order to preclude undesirable burning of tissue proximate the incision.

When performing a cataract extraction, as described above, it is desirous to preclude a loss of fluid from the eye, through leakage around the surgical instrument and through the incision, in order to preserve the eye's volumetric integrity, maintain intraocular pressure and maintain vital ocular structures. Accordingly, it is desirable to maintain a relatively tight seal between the surgical instrument and the incision, to preclude or reduce such loss of fluid. One prior art approach for maintaining this relatively tight seal is disclosed within Sorich, U.S. Pat. No. 4,515,583, which discloses an elliptical sleeve for a phacoemulsification instrument. The elliptical shape of this sleeve attempts to more closely approximate the configuration of the incision through the cornea.

While the elliptical sleeve disclosed within Sorich '583 may at times more closely approximate the incision's configuration, as compared to a fixed, circular sleeve, prior art sleeves such as those disclosed within Sorich '583 are relatively fixed in cross-sectional size, and may not be expanded or contracted in order to accommodate incisions of variable size and variable shape.

Accordingly, it is the object of the present invention to provide a sleeve apparatus for use in combination with a surgical instrument, wherein the sleeve apparatus is expansile in circumference in order to conform to incisions of a wide variety of shapes and sizes.

It is another object of the present invention to provide a method for removing a cataract through an incision in the patient's eye which includes expanding in circumference a surgical sleeve of a surgical instrument, in order to conform the sleeve to the size and shape of incision and/or interior of the wound in the patient's eye.

These and other objects, features, and modes of operation of the present invention will become apparent in light of the present specification, claims, and drawings.

SUMMARY OF THE INVENTION

The present invention comprises a sleeve apparatus for use in combination with a surgical instrument having a distal end for insertion through an incision in the patient's eye and bathing the surgical instrument in irrigation fluid. The sleeve apparatus comprises at least one fluid outlet proximate a distal end portion of the sleeve apparatus. A first sleeve member, having an interior longitudinal bore communicating with the fluid outlet, through which at least a distal end of the surgical instrument is insertable, is provided. The interior longitudinal bore of the first sleeve member operably receives the surgical instrument, so as to create a first chamber therebetween for the irrigation fluid to pass along the surgical instrument to the fluid outlet. A second sleeve member, being substantially concentric to and operably attached to an outer surface of a first sleeve member, is provided to substantially surround a portion of the sleeve member and create a second chamber for receipt of expansion material therebetween. The second sleeve member is expansile in circumference due to the resilient nature of the sleeve material and the presence of expansion material within the second chamber, so as to substantially conform to the shape of the incision and/or the interior of the wound and substantially seal the incision and reduce the loss of fluid from the patient's eye. Delivery means, operably connected to the second sleeve member, are provided for filling the second chamber with any of a variety of expansion materials. Adjustment means, operably associated with the delivery means, are provided for expanding or decreasing the circumference of the second sleeve member. Also provided are attachment means for operably attaching the second sleeve apparatus to the surgical instrument, by such means as an interference fit between the interior surface of the proximate end of the first sleeve and a corresponding exterior surface of the surgical instrument. Alternatively, the interior of the proximate end of the first sleeve can be provided with internal ribs or threads to better engage the instrument.

In a preferred embodiment, the delivery means comprises an expansion material inlet conduit operatively coupled to the second sleeve member and communicating with the second chamber. The expansion material inlet conduit permits the expansion material to be introduced under pressure into the second chamber, so as to expand the circumference of the second sleeve member proportionate to the pressure of the expansion material introduced into the second chamber.

In an alternative embodiment, the placement of the inlet valve may allow the fluid flowing around the phacoemulsification tip into the second chamber to serve as the expansion material.

Also, in a preferred embodiment, the adjustment means comprises a one-way valve operatively attached to the expansion material inlet conduit. The one-way valve permits the expansion material to flow from the expansion material inlet conduit into the second chamber and substantially precludes a reverse flow of expansion material from the second chamber, out through the expansion material inlet conduit. The adjustment means further comprises a pump operatively attached to the expansion material inlet conduit. The pump permits expansion material to be selectively introduced into the expansion material inlet conduit, and, in turn, into the second chamber.

Also, in a preferred embodiment, the adjustment means comprises an expansion material outlet conduit operatively coupled to the second sleeve member and communicating with the second chamber. The expansion material outlet conduit permits at least a portion of the expansion material previously introduced under pressure into the second chamber to be expelled from the second chamber, so as to decrease the prior expansion of the circumference of the second sleeve member. The adjustment means preferably further comprises a bleed valve operatively coupled to the expansion material outlet conduit.

In one preferred embodiment, the bleed valve is manually settable between a substantially open configuration and a substantially closed configuration. The bleed valve permits the expansion material to exit the expansion outlet conduit and, in turn, the second chamber when in the substantially open configuration. The bleed valve substantially precludes expansion material from exiting the expansion material conduit and, in turn, the second chamber when in the substantially closed configuration. In another preferred embodiment, the bleed valve automatically permits at least a portion of the expansion material to exit the expansion material outlet conduit and, in turn, the second chamber, when the pressure of the expansion material within the second chamber and, in turn, the expansion material outlet conduit, exceeds a predetermined quantity of pressure. In a preferred embodiment, the predetermined quantity of pressure is manually presettable.

In another preferred embodiment, the adjustment means further comprises a bleed valve operatively coupled to the second sleeve member and communicating with the second chamber. The bleed valve automatically releases at least a portion of the expansion material from the second chamber when the pressure of expansion material within the second chamber exceeds a predetermined quantity of pressure. In this preferred embodiment, the bleed valve is located proximate the distal end portion of the surgical instrument, such that expulsion of the expansion material from the second chamber in turn releases the expansion fluid into a wound region behind the incision, following insertion of at least a portion of the sleeve apparatus through the incision. The wound region is thereby irrigated with an expansion material, such as an irrigation solution.

In another preferred embodiment, the expansion material is a gas, such as air. However, when the expansion material is a gas, such as air, the expansion fluid is released through a bleed valve located at all times outside the eye and away from the incision. In yet another preferred embodiment, the expansion material is a viscoelastic material.

Also, in a preferred embodiment, the second sleeve member is constructed from a resilient material, such as a silicone rubber material or a thermoplastic material.

In another preferred embodiment, the second sleeve member has a substantially elongated toroidal configuration and an interior second chamber. The second sleeve member is again substantially concentric to and operatively associated with an outer surface of the first sleeve member so as to substantially surround a portion of the first sleeve member. The second sleeve member is expansile in circumference due to the presence of expansion material within the second chamber, so as to substantially conform to the shape of the incision and substantially seal the incision and reduce the loss of fluid from the patient's eye.

In another preferred embodiment, the sleeve apparatus comprises a second sleeve member attachable to the first sleeve member. The second sleeve member is concentric to and operatively associated with an outer surface of the first sleeve member, so as to substantially surround a portion of the first sleeve member upon attachment of the second sleeve member to the first sleeve member. The second sleeve member has a substantially elongated toroidal configuration and an interior second chamber.

The present invention also comprises a method for removing a cataract through an incision in the patient's eye. The method comprises the steps of 1) attaching to a surgical instrument having a distal end a sleeve apparatus including a first sleeve member having an interior longitudinal bore through which at least the distal end of the surgical instrument is insertable. The interior longitudinal bore of the first sleeve member operably receives the surgical instrument so as to create a first chamber therebetween. The second sleeve member is substantially concentric to and operably attached to an outer surface of the first sleeve member, substantially surrounding a portion of the first sleeve member and creating a second chamber for receipt of expansion material therebetween; 2) inserting at least a portion of the distal end of the surgical instrument and, in turn, the sleeve apparatus through an incision in the scleral/corneal junction of the eye, engaging the incision with a portion of the second sleeve member; 3) pressurizing the expansion material into the second chamber, and, in turn, expanding the second sleeve member's circumference, until the circumference substantially conforms to the shape of the incision. This, in turn, substantially precludes loss of fluid from the eye through the incision while the surgical instrument is inserted through the incision; 4) vibrating the surgical instrument to transfer vibrations to the distal end of the surgical instrument to, in turn, emulsify the lens; and 5) removing the emulsified lens through a center bore of the distal end of the surgical instrument.

BRIEF DESCRIPTION OF THE DRAWINGS

FIG. 2 of the drawings is a side sectional view of one embodiment of the present sleeve apparatus attached to a phacoemulsification surgical instrument;

FIG. 3 of the drawings is a side sectional view of another embodiment of the present sleeve apparatus attached to a phacoemulsification surgical instrument;

FIG. 7 of the drawings is a side sectional view of yet another embodiment of the present sleeve apparatus attached to a phacoemulsification surgical instrument;

FIG. 8 of the drawings is a side sectional view of still another embodiment of the present sleeve apparatus attached to a phacoemulsification surgical instrument; and FIG. 9 of the drawings is a side sectional view of the sleeve apparatus of FIG. 2, shown attached to an irrigation/aspiration surgical instrument.

DETAILED DESCRIPTION OF THE DRAWINGS

Figure 1:
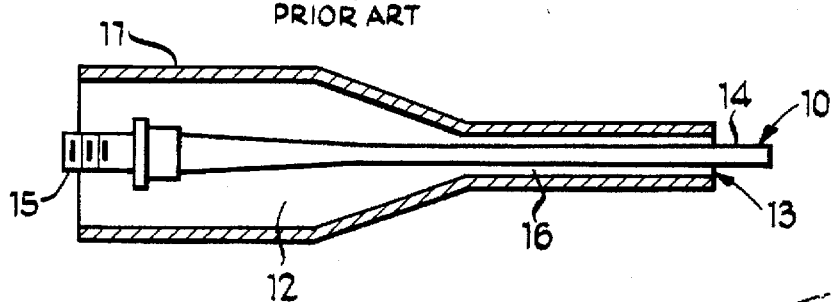
FIG. 1 of the drawings is a side sectional view of a prior art sleeve apparatus attached to a surgical instrument.

While this invention is susceptible of embodiment in many different forms, there is shown in the drawings and will herein be described in detail, several specific embodiments, with the understanding that the present disclosure be considered as an exemplification of the invention and is not intended to limit the invention to the embodiments illustrated.

A prior art sleeve apparatus 11 is shown in FIG. 1. Sleeve 11 includes an interior longitudinal bore 16, through which distal end 14 of surgical instrument 10 is inserted, forming chamber 12 therebetween. Irrigation fluid may be passed, under pressure, through chamber 12, to fluid outlet 13. Sleeve 11 is attached to surgical instrument 10 proximate proximal end 15 of surgical instrument 10. Prior art sleeve 11, which includes a single sleeve, or lumen, may be constructed from either a rigid or flexible material. Sleeve 11 separates surgical instrument 10 from an incision through which surgical instrument 10 and, in turn, sleeve 11 is inserted.

Figure 4:
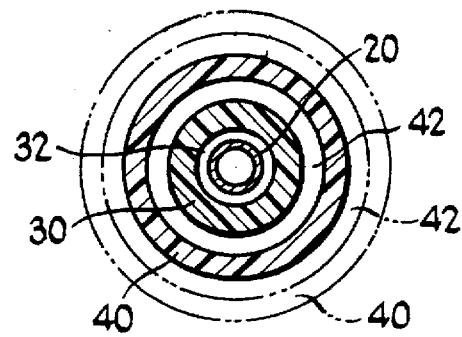
FIG. 4 of the drawings is a cross-sectional view of the sleeve apparatus of FIG. 2, taken generally along lines 4—4 of FIG. 2.

The present sleeve apparatus 25 is shown in FIGS. 2 and 4 as comprising first sleeve member 30 and second sleeve member 40. First sleeve member 30 is preferably constructed from a substantially rigid or semi-flexible material. First sleeve member 30 includes interior longitudinal bore 31 communicating with forward fluid outlet 26. Distal end 21 of surgical instrument 20 is insertable through both interior longitudinal bore 31 and forward fluid outlet 26. Interior longitudinal bore 31 of first sleeve member 30 thus operably receives distal end 21 of surgical instrument 20, creating first chamber 32 therebetween. When distal end 21 of surgical instrument 20 is fully received by first sleeve member 30, distal end 21 extends somewhat beyond a corresponding distal end of sleeve apparatus 25, as shown in FIG. 1.

Surgical instrument 20 comprises a phacoemulsification instrument, including irrigation bores 22, through which irrigation fluid may be pumped under pressure into first chamber 32. First sleeve member 30 further includes side fluid outlets 27, formed through opposing sides of a distal end of sleeve member 30. Irrigation fluid is thus allowed to pass along surgical instrument 20 under pressure, through first chamber 32, to forward fluid outlet 26 and side fluid outlets 27.

Second sleeve member 40 is substantially concentric to and operably attached to a portion of outer surface 33 of first sleeve member 30. Second sleeve member 40 substantially surrounds a portion of first sleeve member 30, creating second chamber 42 therebetween for receipt of expansion material 45. Second sleeve member 40 may be attached by heat sealing or the like; or bonded to first sleeve member 30 with a suitable adhesive.

As shown in FIGS. 2 and 4, second sleeve member 40 is flexible, and expansile in circumference due to the presence of expansion material 45 within second chamber 42, allowing outer surface 43 of second sleeve member 40 to conform to and substantially seal an incision through which surgical instrument 20 is inserted, substantially reducing the loss of fluid from the patient's eye during a lensectomy procedure. Second sleeve member 40 is preferably constructed from a resilient material, such as a silicone rubber or thermoplastic material.

Expansion material inlet conduit 50, operably connected to second sleeve member 40 and communicating with second chamber 42, provides delivery means for filling second chamber 42 with expansion material 45. Expansion material 45 may comprise a gas, such as air. Alternatively, the expansion material may comprise a liquid such as an irrigation solution. The expansion material may also alternatively comprise a viscoelastic material, i.e., a gel, or jelly-like material, such as a hyaronic acid-based material. Two examples of such materials are the HELON™ and VIS-COTE™ brand materials. Expansion material inlet conduit 50 is preferably constructed from a semi-flexible tubing material. One-way valve 60, operatively attached to expansion material inlet conduit 50, permits expansion material to flow from inlet conduit 50 into second chamber 42, while substantially precluding a reverse flow of expansion material from second chamber 42 out through expansion material inlet conduit 50. Pump 61, operatively attached to expansion material inlet conduit 50 and one-way valve 60, permits expansion material 45 to be selectively introduced into expansion material inlet conduit 50 and, in turn, second chamber 42. One-way valve 60 and pump 61 thus collectively provide, adjustment means for expanding the circumference of the second sleeve member.

Pump 61 may be a conventional hand-operated bulb-type pump. Alternatively, pump 61 may be electrically controlled via a hand or foot actuated switch. Pump 61, one-way valve 60, and expansion material inlet conduit 50 accordingly permit expansion material to be introduced under pressure into second chamber 42, expanding the circumference of second sleeve member 40 proportionate to the pressure of expansion material 45 introduced into second chamber 42. Scleral/corneal incisions can vary in size and architecture. A typical incision may vary in length from approximately 3 millimeters (mm) to approximately 7 mm. An incision is typically approximately 3 mm in length when a surgical instrument, such as a phacoemulsification instrument or irrigational/aspiration instrument, is inserted therethrough. The expandability of the second sleeve member accordingly allows the present surgical sleeve apparatus to closely conform to incisions and/or the interior of wounds having a wide variety of sizes and shapes, so as to substantially seal the incision.

In the illustrated embodiments, the second sleeve member is relatively uniform in thickness and composition throughout its length, such that expansion of the second sleeve member, following the introduction of expansion material into the second chamber, is also relatively uniform along the length of the second sleeve member. It is also contemplated, however, that the second sleeve member be constructed of several materials having differing expansile properties, or be constructed so as to have varying thickness of expansile material along its length. In this manner, the second sleeve member may be constructed to provide nonuniform expansion along its length. For example, the second sleeve member may be constructed to provide a substantially conical expanded configuration.

Expansion material outlet conduit 62, operatively coupled to second sleeve member 40 and communicating with second chamber 42, permits at least a portion of expansion material 45 previously introduced under pressure into second chamber to be expelled from second chamber 42, decreasing a prior expansion in circumference of second sleeve member 40. Expansion material outlet conduit 52 is preferably constructed from a semi-flexible tubing material. This is accomplished by bleed valve 63, operatively coupled to and communicating with expansion material outlet conduit 62. Bleed valve 63 may be a conventional valve of the type which is manually switchable, such as by a momentary pushbutton, between a substantially open configuration and a substantially closed (normally) configuration. Bleed valve 63 thus permits expansion material to exit expansion material outlet conduit 62, and, in turn, second chamber 42, when in its substantially open configuration. Conversely, bleed valve 63 substantially precludes expansion material 45 from exiting expansion material outlet conduit 62, and, in turn, second chamber 42, when in its substantially closed configuration.

Alternatively, bleed valve 63 may be of the type which automatically permits at least a portion of expansion material 45 to pass through bleed valve 63 when the pressure of expansion material 45 within second chamber 42 and expansion material outlet 62 exceeds a predetermined quantity of pressure. This predetermined quantity of pressure may be presettable, such as with a dial-type adjuster operatively attached to bleed valve 63.

In this manner, bleed valve 63, cooperating with expansion material outlet conduit 62, provides additional adjustment means for decreasing the circumference of second sleeve member 40, following an expansion of the second sleeve member 40, as previously described. Through the use and interaction of pump 61 and bleed valve 63, the diameter of second chamber 42 may be expanded and contracted to a desired circumference so as to conform to an incision in the eye through which surgical instrument 20 is inserted. Following use of surgical instrument 20, bleed valve 63 may be employed to fully reduce the circumference of second chamber 42, allowing rapid removal of surgical instrument 20 from the incision.

An alternative preferred embodiment of the present invention is shown in FIG. 3. In this preferred embodiment, expansion material outlet conduit 62 (from FIG. 2) is eliminated. Instead, a miniature bleed valve 63' in integrally associated with second sleeve member 40, and communicates directly with second chamber 42. In this preferred embodiment, miniature bleed valve 63' is preferably of the type which automatically permits at least a portion of expansion material 45 to exit miniature bleed valve 63' when the pressure of expansion material 45 within second chamber 42 exceeds a predetermined quantity of pressure. Moreover, inasmuch as, during a lensectomy, expansion material 45 will exit miniature bleed valve 63' into the patient's eye, expansion material 45 in such an embodiment would be a liquid, rather than a gas, inasmuch as the introduction of air into the eye during surgery is undesirable.

Yet another preferred embodiment of the present invention is shown in FIG. 7. In this preferred embodiment, second sleeve member 40' has an elongated toroidal, or elongated donut-like configuration. In this preferred embodiment, second chamber 42' is formed entirely within second sleeve member 40', which now comprises a self-contained balloon or bladder, rather than being formed by the concentric attachment of second sleeve member 40 to first sleeve member 30, as in the previously described embodiments. As in the previously-described embodiments, a suitable adhesive may be employed to attach second sleeve member 40' to first sleeve member 30, or such attachment may be by heat sealing or the like. As with the previously described embodiments, pump 61, one-way valve 60 and expansion material inlet conduit 50 are employed to introduce expansion material 45 into second chamber 42', so as to increase the circumference of second sleeve member 40' to a desired size. Moreover, as in the previously described embodiments, expansion material outlet conduit 62 and bleed valve 63 permit expansion material previously introduced under pressure into second chamber 42' to be selectively removed, thereby decreasing the circumference of second sleeve member 40'.

Still another preferred embodiment of the present invention is shown in FIG. 8. In this preferred embodiment, expansion material outlet conduit 62 and bleed valve 63 have been removed from the embodiment of FIG. 7. Instead, in this preferred embodiment, a miniature bleed valve 63' is operably attached directly to second sleeve member 40', communicating with second chamber 42'. In this preferred embodiment, miniature bleed valve 63' is preferably of the type which automatically permits expansion material to exit miniature bleed valve 63' and, in turn, second chamber 42', when the pressure of expansion material within second chamber 42' exceeds a predetermined quantity of pressure. Moreover, inasmuch as expansion material exiting miniature bleed valve 63' will enter a patient's eye during surgery, expansion material 45, in this preferred embodiment, is preferably an irrigation liquid or viscoelastic material, inasmuch as the introduction of air into the eye during a lensectomy is undesirable.

FIG. 9 shows the present surgical sleeve apparatus of FIG. 1, attached to an irrigation/aspiration surgical instrument 20', rather than a phacoemulsification surgical instrument 20. As shown in FIG. 9, irrigation/aspiration instrument 20' includes central bore 23, through which irrigation fluid may be pumped under pressure into first chamber 32. Surgical instrument 20' includes a rounded distal tip 28, and a side aperture 29.

As shown in FIGS. 2, 3, 7, 8 and 9, a portion of the interior surface of first sleeve member 30 includes threads 75, and a corresponding portion of the exterior surface of surgical instruments 20 and 20' each include threads 76. Sleeve apparatus 25 is accordingly securely attachable to surgical instruments 20 and 20' through threaded attachment, with threads 75 and 76 mating in a manner sufficient to substantially preclude leakage of irrigation fluid from first chamber 32 out through the mated threads.

In each of the illustrated embodiments, one end of the second sleeve member extends to approximately midway along a conical portion of the first sleeve member. It is also contemplated, however, that the second sleeve member may be of various lengths. For example, the second sleeve member may extend along the conical portion of the first sleeve member to a greater or lesser degree than in the illustrated embodiments. Moreover, the second sleeve member may be of a sufficiently shortened length so as to terminate prior to engaging a conical portion of the first sleeve member.

Although, in the illustrated embodiments, the fluid inlet valve is coupled to an outer surface of the second sleeve member via an expansion material inlet conduit, other configurations are also contemplated. For example, in an alternative embodiment, the expansion material inlet conduit may be removed. In this alternative embodiment, the one-way inlet valve is operably positioned between the first and second sleeve members, communicating with both the first and second chambers. The pressurization of expansion material within the first chamber causes a portion of the expansion material to pass through the one-way inlet valve, so as to enter the second chamber and inflate the second sleeve member. The remainder of expansion material within the first chamber will flow towards the forward fluid outlet, exiting the side fluid outlets.

Although, in the preferred embodiments, sleeve apparatus 25 is attachable to surgical instruments 20 and 20' via a threaded attachment, other attachment means are also contemplated, including the use of a press-fit or interference fit, or the use of corresponding ribbed members on the interior of sleeve apparatus 25 and the exteriors of surgical instruments 20 and 20'.

Figure 5:
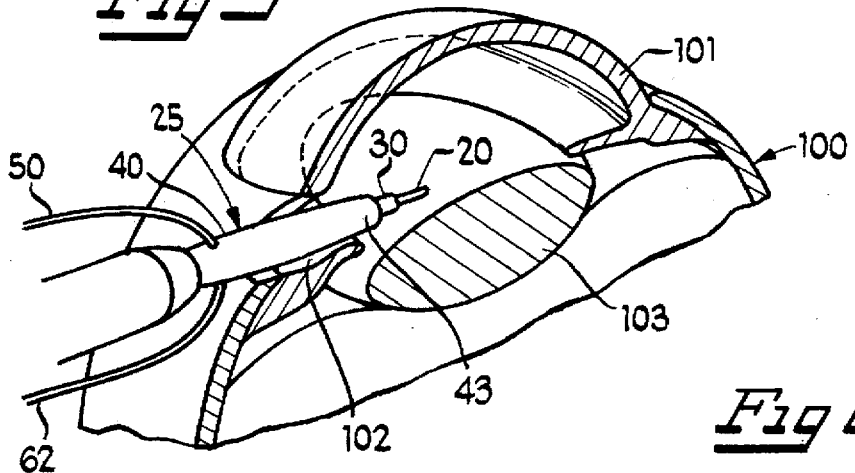
FIG. 5 of the drawings is an enlarged, perspective view of a human eye, partially in section, showing the sleeve apparatus of FIG. 2 inserted through an incision, with the second sleeve member in a non-expanded configuration.
Figure 6:
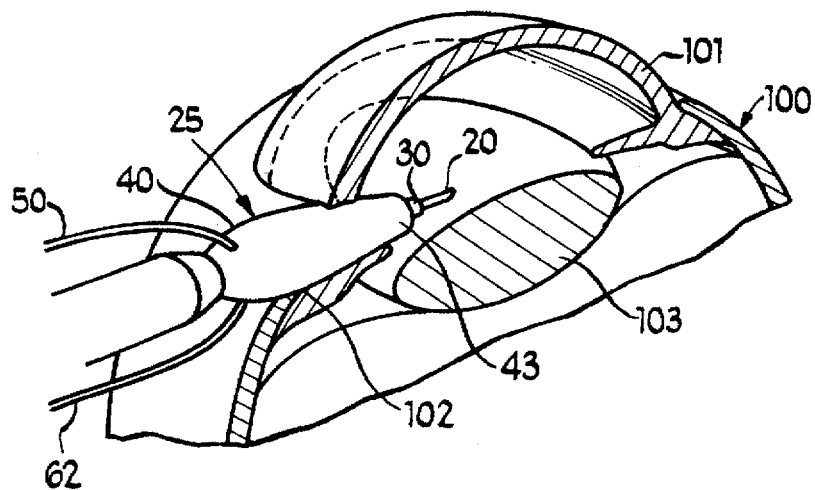
FIG. 6 of the drawings is an enlarged, perspective view of a human eye, partially in section, showing the sleeve apparatus of FIG. 2 inserted through an incision, with the second sleeve member expanded to conform to the shape of the incision.

The removal of a cataract through an incision in a patient's eye is shown in FIGS. 5 and 6. First, (as shown in FIG. 2), sleeve apparatus 25 is attached to phacoemulsification instrument 20, with distal end 21 of phacoemulsification instrument 20 inserted through longitudinal bore 31 of first sleeve member 30. Second chamber 42 is substantially uninflated at this time. Next, as shown in FIG. 5, at least a portion of distal end 21 of phacoemulsification instrument 20, and, in turn, sleeve apparatus 25, is inserted through incision 102 through the scleral/corneal junction 101 of the patient's eye 100, engaging incision 102 with a portion of outer surface 43 of second sleeve member 40. Next, using pump 61 (FIG. 2), expansion material is pressurized into second chamber 42, expanding the circumference of second sleeve member 40, until the outer surface 43 substantially abuts and conforms to incision 102, as shown in FIG. 6. The flexible and expansile properties of the second sleeve member allows the present surgical sleeve apparatus to conform to a wide variety of incisions, of various sizes and configurations. This substantially precludes loss of fluid from eye 100 through incision 102 while phacoemulsification instrument 20 is inserted through incision 102.

Next, phacoemulsification instrument 20 is vibrated, so as to transfer vibrations, such as ultrasonic vibrations, to distal end 21 and, in turn, lens 103. This vibration, in turn, emulsifies lens 103, allowing the emulsified lens to be removed, under vacuum pressure, through a central bore of distal end 21 of phacoemulsification instrument 20. Next, expansion material 45 is bled from second chamber 42, out through expansion material outlet conduit 62 and bleed valve 63, permitting second sleeve member 40 to be reduced in circumference, for subsequent removal of phacoemulsification instrument 20 from incision 102.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A sleeve apparatus in combination with a surgical instrument, the combination comprising:
    a surgical instrument, having a distal end for insertion through an incision in the patient's eye and bathing said distal end of said surgical instrument in irrigation fluid,
    a sleeve apparatus having at least one fluid outlet proximate a distal end portion of said sleeve apparatus; and
    a first sleeve member having an interior longitudinal bore communicating with said at least one fluid outlet, through which a distal end of said surgical instrument is insertable;
    said interior longitudinal bore of said first sleeve member operably receiving said surgical instrument so as to create a first chamber therebetween for said irrigation fluid to pass along said surgical instrument to said fluid outlet;
    said sleeve apparatus further including a second sleeve member being concentric to and operatively attached to an outer surface of said first sleeve member, so as to surround a portion of said first sleeve member and create a second chamber capable of receiving an expansion material therebetween;
    said second sleeve member, having a circumference and capable of being expansile in circumference, upon introduction of an expansion material within said second chamber so as to enable the second sleeve member to conform to the shape of the incision and substantially seal the incision and reduce the loss of fluid from the patient's eye;
    said combination further including delivery means operably connected to said second sleeve member for enabling the filling said second chamber with an expansion material; and
    adjustment means operably associated with said delivery means for modifying said circumference of said second sleeve member; and,
    attachment means for operably attaching said sleeve apparatus to said surgical instrument, said attachment means further including means for fixedly attaching said first sleeve member to a portion of said surgical instrument, to preclude longitudinal movement of said first sleeve member relative to said surgical instrument.

2. The invention according to claim 1, wherein said delivery means comprises an expansion material inlet conduit operatively coupled to said second sleeve member and communicating with said second chamber, said expansion material inlet conduit permitting an expansion material to be introduced under pressure into said second chamber so that when an expansion material is introduced under pressure, the circumference of said second sleeve member will expand proportionately to the pressure at which an expansion material is introduced.

3. The invention according to claim 2, wherein said adjustment means comprises:
    a one-way valve operatively attached to said expansion material inlet conduit, said one-way valve permitting an expansion material to flow from said expansion material inlet conduit into said second chamber and substantially precluding a reverse flow of expansion material from said second chamber out through said expansion material inlet conduit, when expansion material is present within the second chamber; and
    a pump operably attached to said expansion material inlet conduit, said pump permitting expansion material to be selectively introduced into said expansion material conduit and, in turn, into said second chamber.

4. The invention according to claim 2, wherein said adjustment means comprises an expansion material outlet conduit operatively coupled to said second sleeve member and communicating with said second chamber, said expansion material outlet conduit permitting an expansion material, which has been previously introduced under pressure into said second chamber, to be expelled from said second chamber, so as to decrease a prior expansion of said circumference of said second sleeve member.

5. The invention according to claim 4, wherein said adjustment means further comprises a bleed valve operatively coupled to said expansion material outlet conduit.

6. The invention according to claim 5, wherein said bleed valve is manually settable between an open configuration and a closed configuration, said bleed valve permitting an expansion material, when present in said second chamber, to exit said expansion material outlet conduit and, in turn, said second chamber when in said open configuration, and precluding expansion material, when present in said second chamber, from exiting said expansion material conduit and, in turn, said second chamber when in said closed configuration.

7. The invention according to claim 5, wherein said bleed valve is configured to automatically permit expansion material, when present in said second chamber, to exit said expansion material outlet conduit and, in turn, said second chamber when the pressure of expansion material, when present in said second chamber, and, in turn, said expansion material outlet conduit, exceeds a predetermined quantity of pressure.

8. The invention according to claim 7, wherein said predetermined quantity of pressure is manually presettable.

9. The invention according to claim 4, wherein said adjustment means further comprises a bleed valve operatively coupled to said second sleeve member and communicating with said second chamber, said bleed valve permitting expansion material, which has been previously introduced under pressure into said second chamber to be expelled from said second chamber, so as to decrease prior expansion of said circumference of said second sleeve member.

10. The invention according to claim 9, wherein said bleed valve automatically permits expansion material, which has been previously introduced under pressure into said second chamber, to be expelled from said second chamber when the pressure of expansion material, which has been previously introduced under pressure into said second chamber, exceeds a predetermined quantity of pressure.

11. A sleeve apparatus in combination with a surgical instrument, the combination comprising:

a surgical instrument, having a distal end for insertion through an incision in the patient's eye and bathing said distal end of said surgical instrument in irrigation fluid;

at least one fluid outlet proximate a distal end portion of said sleeve apparatus;

a first sleeve member having an interior longitudinal bore communicating with said at least one fluid outlet, through which a distal end of said surgical instrument is insertable;

said interior longitudinal bore of said first sleeve member operably receiving said surgical instrument so as to create a first chamber therebetween for said irrigation fluid to pass along said surgical instrument to said fluid outlet;

a second sleeve member being concentric to and operatively attached to an outer surface of said first sleeve member, so as to surround a portion of said first sleeve member and create a second chamber for receipt of an expansion material therebetween;

said second sleeve member, having a circumference and being expansile in circumference when an expansion material is introduced within said second chamber so as to conform to the shape of the incision and substantially seal the incision and reduce the loss of fluid from the patient's eye;

delivery means operably connected to said second sleeve member and a supply of expansion material for filling said second chamber with said expansion material;

adjustment means operably associated with said delivery means for modifying said circumference of said second sleeve member; and, attachment means for operably attaching said sleeve apparatus to said surgical instrument;

the delivery means including an expansion material inlet conduit operably coupled to said second sleeve member and communicating with said second chamber, said expansion material inlet conduit permitting said expansion material to be introduced under pressure into said second chamber so as to expand said circumference of said second sleeve member proportionate to said pressure of said expansion material introduced into the second chamber;

said adjustment means including an expansion material outlet conduit operatively coupled to said second sleeve member and communicating with said second chamber, said expansion material outlet conduit permitting said expansion material previously introduced under pressure into said second chamber to be expelled from said second chamber, so as to decrease said prior expansion of said circumference of said second sleeve member;

said adjustment means further including a bleed valve operatively coupled to said second sleeve member and communicating with said second chamber, said bleed valve permitting said expansion material previously introduced under pressure into said second chamber to be expelled from said second chamber, so as to decrease said prior expansion of said circumference of said second sleeve member;

said bleed valve automatically permitting said expansion material to be expelled from said second chamber when said pressure of said expansion material within said second chamber exceeds a predetermined quantity of pressure;

said bleed valve further being located proximate said distal end portion of said surgical instrument, such that expelling said expansion material from said second chamber in turn releases said expansion fluid into a wound region behind said incision, following insertion of at least a portion of said sleeve apparatus through said incision, thereby irrigating said wound region with said expansion material.

12. The invention according to claim 11, wherein said expansion material is a liquid.

13. The invention according to claim 12, wherein said liquid is an irrigation solution.

14. The invention according to claim 11, wherein said expansion material is a gas.

15. The invention according to claim 14, wherein said gas is air.

16. A sleeve apparatus in combination with a surgical instrument, the combination comprising:

a surgical instrument, having a distal end for insertion through an incision in the patient's eye and bathing said distal end of said surgical instrument in irrigation fluid;

at least one fluid outlet proximate a distal end portion of said sleeve apparatus;

a first sleeve member having an interior longitudinal bore communicating with said at least one fluid outlet, through which a distal end of said surgical instrument is insertable;

said interior longitudinal bore of said first sleeve member operably receiving said surgical instrument so as to create a first chamber therebetween for said irrigation fluid to pass along said surgical instrument to said fluid outlet;

a second sleeve member being concentric to and operatively attached to an outer surface of said first sleeve member, so as to surround a portion of said first sleeve member and create a second chamber for receipt of an expansion material therebetween;

said second sleeve member having a circumference and being expansile in circumference when an expansion material is introduced within said second chamber so as to conform to the shape of the incision and substantially seal the incision and reduce the loss of fluid from the patient's eye;

delivery means operably connected to said second sleeve member and a supply of expansion material for filling said second chamber with said expansion material;

adjustment means operably associated with said delivery means for modifying said circumference of said second sleeve member; and, attachment means for operably attaching said sleeve apparatus to said surgical instrument; and said expansion material being a viscoelastic material.

17. The invention according to claim 16, wherein said second sleeve member is constructed from a resilient material.

18. The invention according to claim 17, wherein said resilient material is a silicone rubber material.

19. The invention according to claim 17, wherein said resilient material is a thermoplastic material.

20. A sleeve apparatus in combination with a surgical instrument, the combination comprising:

a surgical instrument having a distal end for removing a cataract through an incision in a patient's eye and continuous bathing said surgical instrument in irrigation fluid; and a sleeve apparatus having at least one fluid outlet proximate a distal end portion of said sleeve apparatus; and a first sleeve member having an interior longitudinal bore communicating with said at least one fluid outlet, through which a distal end of said surgical instrument is insertable;

said interior longitudinal bore of first sleeve member operably receiving said surgical instrument so as to create a first chamber therebetween for said irrigation fluid to pass along said surgical instrument to said fluid outlet;

said sleeve apparatus further including a second sleeve member being concentric to and operatively associated with an outer surface of said first sleeve member so as to surround a portion of said first sleeve member;

said second sleeve member having a substantially elongated toroidal configuration and an interior second chamber;

said second sleeve member having a circumference and being expansile in circumference when an expansion material is introduced within said second chamber so as to conform to the shape of the incision and substantially seal the incision and reduce the loss of fluid from the patient's eye;

said combination further including delivery means operably connected to said second sleeve member and a source of expansion material for filling said second chamber with said expansion material;

adjustment means operably associated with said delivery means for modifying said circumference of said second sleeve member; and, attachment means for operably attaching said sleeve apparatus to said surgical instrument, said attachment means further including means for fixedly attaching said first sleeve member to a portion of said surgical instrument, to preclude longitudinal movement of said first sleeve member relative to said surgical instrument.

21. A sleeve apparatus in combination with a surgical instrument, said surgical instrument having a distal end for removing a cataract through an incision in the patient's eye and continuously bathing said surgical instrument in irrigation fluid, at least one fluid outlet proximate said distal end portion of said surgical instrument, and a first sleeve member having an interior longitudinal bore communicating with said at least one fluid outlet, through which said distal end of said surgical instrument is insertable, said interior longitudinal bore of said first sleeve member operably receiving said surgical instrument so as to create a first chamber therebetween for said irrigation fluid to pass along said surgical instrument to said fluid outlet, said combination further comprising:

a second sleeve member attachable to said first sleeve member, said second sleeve member being concentric to and operatively associated with an outer surface of said first sleeve member so as to surround a portion of said first sleeve member upon attachment of said second sleeve member to said first sleeve member, said second sleeve member having a substantially elongated toroidal configuration and an interior second chamber;

delivery means operably connected to said second sleeve member and a source of expansion material, for filling said second chamber with said expansion material; and adjustment means operably associated with said delivery means for modifying said circumference of said second sleeve member, said attachment means further including means for fixedly attaching said first sleeve member to a portion of said surgical instrument, to preclude longitudinal movement of said first sleeve member relative to said surgical instrument.

22. A method for removing a cataract through an incision in the patient's eye, said method comprising the steps of:

attaching to a surgical instrument having a distal end a sleeve apparatus including a first sleeve member having an interior longitudinal bore through which said distal end of said surgical instrument is insertable, said interior longitudinal bore of said first sleeve member operably receiving said surgical instrument so as to create a first chamber therebetween, and a second sleeve member concentric and operably attached to an outer surface of said first sleeve member so as to surround a portion of said first sleeve member and create a second chamber for receipt of expansion material therebetween;

inserting said distal end of said surgical instrument and, in turn, said sleeve apparatus through an incision in the scleral/corneal junction of said eye, engaging said incision with a portion of said second sleeve member;

pressurizing said expansion material into said second chamber, and, in turn, expanding a circumference of said second sleeve member, until said circumference conforms to said incision, substantially precluding loss of fluid from said eye through said incision while said surgical instrument is inserted through said incision;

vibrating said surgical instrument to transfer vibrations to said distal end of said surgical instrument to, in turn, emulsify a lens of the patient's eye; and removing an emulsified lens through a central bore of said distal end of said surgical instrument by applying vacuum pressure to said central bore.

23. An apparatus for use in surgical procedures, having a distal end for insertion through an incision in a patient's eye, said apparatus comprising:

an elongated inner member, having a longitudinal aperture therethrough for enabling a surgical instrument to be insertably received therethrough;

a sleeve member operatively attached to an outer surface of said elongated inner member, so as to surround a portion of said elongated inner member and create a chamber therebetween;

said sleeve member expanding upon the introduction of an expansion material within said chamber so as to conform to the shape of the incision; and delivery means operably connected to said sleeve member for introducing an expansion material into said chamber;

means for fixedly attaching said elongated inner member to a portion of said surgical instrument, to preclude longitudinal movement of said elongated inner member relative to said surgical instrument.

24. An apparatus for use in a surgical procedure, having a distal end for insertion through an incision in a patient's eye, said apparatus comprising:

an elongated inner member, having a longitudinal aperture therethrough for inserting receipt of a surgical instrument;

a sleeve member operatively associated with an outer surface of said elongated inner member so as to surround a portion of said elongated inner member;

said sleeve member having a substantially elongated toroidal configuration and an interior chamber;

said sleeve member expanding upon the introduction of an expansion material into said interior chamber so as to conform to the shape of the incision; and delivery means operably connected to said sleeve member for introducing an expansion material into said interior chamber;

means for fixedly attaching said elongated inner member to a portion of said surgical instrument, to preclude longitudinal movement of said elongated inner member relative to said surgical instrument.

* * * * *